US005232697A

United States Patent [19]

Bahrani

[11] Patent Number: 5,232,697

[45] Date of Patent: * Aug. 3, 1993

[54] PROCESSES FOR CLEANING PSYLLIUM SEEDS

[75] Inventor: Abdul S. Bahrani, Cincinnati, Ohio

[73] Assignee: The Procter & Gamble Company, Cincinnati, Ohio

[*] Notice: The portion of the term of this patent subsequent to Jun. 4, 2008 has been disclaimed.

[21] Appl. No.: 879,503

[22] Filed: May 1, 1992

Related U.S. Application Data

[60] Continuation of Ser. No. 666,152, Mar. 7, 1991, abandoned, which is a division of Ser. No. 374,405, Jun. 30, 1989, Pat. No. 5,020,732.

[51] Int. Cl.5 ...................... A61K 35/78; B02C 19/12; A23L 1/10

[52] U.S. Cl. ................................ 424/195.1; 426/482; 241/7; 241/188.1; 241/188.2; 99/600; 99/602; 99/603

[58] Field of Search ............ 424/195.1; 241/7, 188 A; 99/600, 602, 603; 426/482

[56] References Cited

U.S. PATENT DOCUMENTS

| | | | |
|---|---|---|---|
| 901,217 | 10/1908 | Touya | 241/188 A |
| 2,428,670 | 10/1947 | Hulse | 241/188 A |
| 3,219,286 | 11/1965 | Doyle | 241/188 A |
| 3,717,480 | 2/1973 | Guichard et al. | 99/233.3 |
| 4,292,890 | 10/1981 | Salete-Garces | 99/603 |
| 4,511,561 | 4/1985 | Madaus | 424/195.1 |
| 4,583,455 | 4/1986 | Salete-Garces | 99/519 |
| 4,689,229 | 8/1987 | Banik | 424/195.1 |
| 4,813,613 | 3/1989 | Salete | 241/7 |
| 5,048,760 | 9/1991 | Barbera | 241/9 |

FOREIGN PATENT DOCUMENTS

| | | |
|---|---|---|
| 3707568 | 7/1988 | Fed. Rep. of Germany . |
| 2616329 | 12/1988 | France . |
| 672229 | 5/1952 | United Kingdom . |
| 2224628A | 5/1990 | United Kingdom . |

OTHER PUBLICATIONS

Modern Stud Mills, Type Molloplex and Contraplex Optimum Fineness-Economic Energy Consumption Leaflet 10-11/3e, Alpine American Corp. Natick, Mass.

"Fluidized Bed Opposed Jet Mills AFG Model 100-1250" Leaflet 21/IUS Alpine American Corp. Natick, Mass.

Gopani, "Isubgol Cultivation in India", Farm Bulletin, pp. 1-18 (1969; published by the Farm Information Unit, Directorate of Extension, Ministry of Food, Agriculture, Community Development and Cooperation, New Delhi, India).

Makarenko et al., Farm Zh, Jun., 1980, (3), pp. 77-78.

*Primary Examiner*—Michael G. Wityshyn
*Assistant Examiner*—Ralph Gitomer
*Attorney, Agent, or Firm*—Kim William Zerby; Douglas C. Mohl; Richard C. Witte

[57] ABSTRACT

Processes for dehusking psyllium seeds to obtain high yields of high purity psyllium seed husk. These processes comprise milling intact psyllium seeds in a mill which causes the husk to be fragmented by collision under conditions whereby the husk is fractured and separated from the non-husk portion of the psyllium seed without substantial breakage and size reduction of the non-husk portion. Preferred milling utilizes impact speeds within the range of from about 5 m/sec to about 40 m/sec.

8 Claims, No Drawings

PROCESSES FOR CLEANING PSYLLIUM SEEDS

This is a continuation of application Ser. No. 666,152 filed Mar. 7, 1991, now abandoned, which is a division of application Ser. No. 374,405, filed on Jun. 30, 1989, now U.S. Pat. No. 5,020,732, issued Jun. 4, 1991.

BACKGROUND OF THE INVENTION

The present invention relates to processes for dehusking psyllium seeds. These processes are useful for obtaining high yields of high purity psyllium seed husk.

The seed to be dehusked by the processes of the present invention is psyllium seed from plants of the Plantago genus. Various species such as Plantago lanceolate, P. rugelii, and P. major are known. Commercial psyllium seed husk is typically obtained from the French (black; Plantago indica), Spanish (P. psyllium) or Indian (blonde; P. ovata) psyllium seeds. Indian (blonde) psyllium seed husk is preferably prepared by the present processes.

Psyllium seed husk is used in high fiber food products and/or health care products for its benefit of normalizing bowel function and laxation. In addition, recent research has demonstrated the effectiveness of psyllium seed husk fiber in reducing human serum cholesterol levels, and in controlling blood glucose levels in diabetics. Observed and anticipated growth in the markets for these psyllium husk-containing products give rise to the need for greater quantities of high purity psyllium husk. Thus, there is a need for processes for obtaining higher yields of high purity psyllium husk that are more efficient than the currently used methods.

Psyllium seed husk is typically manufactured presently by separating the seed husk from the remainder of the seed by slight mechanical pressure, for example by crushing the seeds between rotating plates or rollers. The husk is then typically purified by sieving the mixture to separate the husk from the remainder of the seed parts and/or by blowing (winnowing) the husk away from the impurities. Impurity present in the psyllium husk is predominantly dark particles which are readily visually apparent amongst the blond-colored psyllium husk; and are readily perceived as being particularly gritty during ingestion. Subsequent attempts at purifying the psyllium further, for example by sieving, are generally tedious processes which produce low yields of psyllium and/or only moderately improved purity.

Mills suitable for the processes of the present invention are known. Generally, they are characterized as being mills which produce fragmentation (i.e., the "milling") of materials through collision, including particle-particle collision (e.g., fluid energy mills) and/or particle-blunt surface collision (e.g., stud mills; ball mills), rather than having the fragmentation being caused solely by a crushing action or by scissoring, screening, abrading, shearing, or slicing actions.

Such mills have been used to mill a wide variety of materials. For example, materials such as silica gel, tungsten carbide, toner, wax, resin, fat, and mica have been milled in fluidized bed opposed jet mills; and materials such as acetyl salicylic acid, bran, sesame seeds, glucose, grains, and copper oxychloride have been milled in stud mills. Furthermore, selective grinding by fluidized bed opposed jet mills during the processing of foundry sand (to separate water glass bond or resin cement from the sand) and the cleaning of metal alloys (to separate mineral or ceramic contaminants from the main alloy) are known.

An object of the present invention is to provide processes for dehusking psyllium seeds without substantial breakage and size reduction of the non-husk core of the psyllium seed. Such processes are useful for manufacturing high yields of high purity psyllium seed husk from whole psyllium seeds. A further object is to provide processes for removing the psyllium seed husk from whole psyllium seed while avoiding breaking the core of the seed, thereby reducing contamination of the husk with non-husk seed parts (resulting in higher purity due to easier separation of husk and non-husk seed parts). Another object is to provide processes for obtaining psyllium husk and non-husk mixtures which are easily separated by density, particle size and/or shape separation methods (e.g., sieving; screening) into husk and non-husk fractions having little contamination by the other fraction's components. It is also an object to provide efficient, low energy processes for manufacturing psyllium seed husk.

These and other objects of the present invention will become readily apparent from the detailed description which follows.

All percentages and ratios used herein are by weight unless otherwise specified. Screen mesh sizes used herein are based on U.S. standards.

SUMMARY OF THE INVENTION

The present invention relates to processes for dehusking psyllium seed. These processes comprise the steps of: (a) milling intact psyllium seeds in a mill which causes the husk to be fragmented by collision under conditions whereby the husk is fractured and separated from the non-husk portion of the psyllium seed without substantial breakage and size reduction of the non-husk portion; and (b) collecting the milled psyllium seed husk and non-husk mixture. Preferably, the conditions whereby the husk is fractured and separated from the non-husk portion of the psyllium seed is achieved by impacting the seed at an impact speed of from about 5 m/sec to about 40 m/sec (more preferably from about 1 Om/sec to about 35 m/sec; and most preferably from about 10 m/sec to less than about 30 m/sec).

The present invention also relates to processes for obtaining purified psyllium seed husk. These processes comprise the steps of: (a) dividing dehusked psyllium seed mixture, prepared by a dehusking process as described herein, into one or more fragments enriched with non-husk material and one or more fragments enriched with husk; and (b) collecting the fragments enriched in psyllium husk.

DETAILED DESCRIPTION OF THE INVENTION

In contrast to the art-known methods of grinding or milling seed husk solely by crushing the seed (e.g., between plates, abrasive grinding wheels, or rollers) or "slicing" the husk (e.g., by cutting, scissoring, abrading, or shearing against sharp blades, screens, grates, etc.), it has been discovered that it is possible to remove the husk from the remainder of the psyllium seed without disintegrating the non-husk seed core part. This is achieved by employing certain levels of collision force in the milling process to fracture psyllium seed husk and concomitantly dislodge the husk from the non-husk psyllium seed core under conditions whereby the non-husk psyllium seed core is not likewise fractured. The result of this process is a mixture containing psyllium seed husk and essentially intact non-husk psyllium seed core. Size, density and/or shape of the fragmented husk in comparison to the unfragmented non-husk core component permits simple, high yield, efficient separation of these components to obtain high purity psyllium seed husk having very low amounts of non-husk seed parts.

As noted hereinbefore, mills suitable for the psyllium seed dehusking processes of the present invention are known. Generally, they are characterized as being mills which produce fragmentation (i.e., the "milling") of the material solely or predominantly through collision (impacting), including particle-particle collision and/or particle-blunt surface collision, rather than having the fragmentation being caused by solely a crushing or slicing action. It is highly desirable that such mills permit control of the impact force exerted on the seed so as to be able to effectively minimize the potential for breaking the seed core along with the husk.

An example of one type of suitable mill, preferred for the processes of the present invention, is known as "stud mills" (also known as "pin mills"). Stud mills are generally described as mills which grind by impact of the material against round pins or "studs" which are moving at high speed. These pins are located in rows forming concentric circles. Several concentric circles of pins are placed on a rotor. These rotor pins are additionally placed concentric with a similar arrangement on a stator or second rotor. In the two rotor arrangement, they rotate in opposite directions. Psyllium seeds passing through the zone of rotating pins is subjected to many collisions with the pins and with other particles, thereby resulting in dehusking of the seed.

Commercially available stud mills include Kolloplex® Stud Mills (one rotating, one stationery stud disc; sold by Alpine American Corp., Natick, Mass.); Contraplex® Stud Mills (two Mass.); and Centrimil® (sold by Entoleter, Inc.; New Haven, Conn.). Specific examples include the Kolloplex® Stud Mills Type 250 Z, 400 Z, and 630 Z; the Kolloplex® Laboratory Mill 160 Z; the Contraplex® Stud Mills Type 250 CW, 400 CW, 630 C, 710 CW, and 1120 CW; the Contraplex® Laboratory Mill 63 C; and the Series 18 Centrimil. Certain of these stud mills are described in more detail in Leaflet 10-11/3e (titled "Modern Stud Mills") available from Alpine American Corp. and incorporated by reference herein in its entirety.

An example of another type of mill useful for the process of the present invention is fluid energy mills. These mills generally operate by the process of particle-particle collisions. Psyllium seed to be dehusked is introduced into the mill through a venturi feeder. The material contacts air, steam, or other gas moving at sonic and supersonic velocities. This causes the seeds to be accelerated and to collide with other seeds/particles, and dehusking occurs. The dehusked psyllium seed mixture is carried out with the exit air and/or collected in batches.

Commercially available fluid energy mills include Fluidized Bed Opposed Jet Mills (sold by Alpine American Corp., Natick, Mass.). Specific examples include the Fluidized Bed Jet Mills 100 AFG, 200 AFG, 400 AFG, 630 AFG, 800 AFG, and 1250 AFG, all sold by Alpine American Corp. These fluidized bed mills are described in more detail in Leaflet 21/IUS (titled "Fluidized Bed Opposed Jet Mills AFG") available from Alpine American Corp. and incorporated by reference herein in its entirety.

An example of another type of mill useful for the processes of the present invention is "ball mills" (also known as "pot mills" or "Jar mills"). These mills generally operate by the process of attrition and impact, the milling being effected by placing the substance in jars or cylindrical vessels, lined with porcelain or a similar hard substance and containing "pebbles" or "balls" of flint, porcelain, steel, or stainless steel. These cylindrical vessels revolve horizontally on their long axis and the tumbling of the pebbles or balls over one another and against the sides of the cylinder effects dehusking. A variation of this type of mill is the "vibrating ball mills", which also combine attrition and impact, consisting of a mill shell containing a charge of balls similar to the previously described ball mills. However, these mills vibrate the shell rather than rotate. Commercially available vibrating ball mills include the Sweco Vibro Energy Grinding Mill Model DM1.

The specific impact milling conditions (e.g., feed rate of the intact psyllium seed into the mill; pin density; rpm of the mill) for removing the husk without disintegrating the non-husk core component is expected to vary according to the particular batch of seeds being processed (influenced by, for example, moisture content, age, or species of seed), and the specific piece of equipment utilized. Optimization of the process can be readily achieved by simple experimentation and evaluation of the yield and purity of the husk being obtained. Selection of the process conditions for specific applications are readily made by one skilled in the art. However, as further guidance in selecting the appropriate conditions, it is suggested to consider using impact speeds within the range of from about 5 m/sec to about 40 m/sec.

For example, the process conditions relating to impact speed were evaluated using a sample of P. ovata (Indian blonde psyllium) seed using a stud mill (single pass milling in an Entoleter Centrimil as described more fully in the Example hereinafter). Under these conditions it was determined that an impact speed in the range of at least about 5 m/sec to 1Om/sec will fracture and dislodge the husk from the psyllium seed. Furthermore, an impact speed of about 40 m/sec not only fractures and dislodges the husk, but is also sufficiently forceful to disintegrate a portion of the non-husk seed part. A distinct increase in single pass yields and decrease in husk purity was observed at impact speeds above about 36 m/sec as a result of significant increase in the amount of disintegration of seed cores under these conditions.

Thus, operating within the range of from about 5 m/sec to about 35 m/sec (preferably within from about 1Om/sec to less than about 30 m/sec) permits multiple passes of the psyllium seeds and dehusked psyllium seed cores through the mill without the necessity of separating the dehusked seed cores from the intact seed prior to remilling. When impact speeds are within the range of from about 35 m/sec to about 40 m/sec (preferably within from about 30 m/sec to 40 m/sec), it is viewed as desirable to separate the dehusked seed cores from the intact seeds after each pass, or only a very few number of passes, through the mill. (The term "multiple pass" or "multiple passes", as used herein, means remilling intact psyllium seeds without separating dehusked seed cores from the intact seeds.) While multiple passes of the psyllium seed through the mill are possible with impact speeds within the range of about 5 m/sec to about 35 m/sec, for purposes of optimization of yield and minimizing non-husk seed disintegration (and thus simplifying separation and reducing impurity), impact speeds in the range of from about 10 m/sec to less than about 30 m/sec are preferred. The higher the impact speed, the fewer passes typically needed to obtain good yields. Obviously, it is not necessary that each pass operate at the same impact speed, and the total process may involve a combination of single and multiple pass milling between collection and/or separation steps if desired.

The processes of the present invention include simply milling the intact psyllium seed and collecting the resulting mixture of psyllium husk and substantially intact non-husk core. This mixture may then be stored for later separation of the husk from the non-husk fraction, or for shipment to another processor who will separate and collect the psyllium husk as described hereinafter. However, it is preferred that the processes of the present invention include a step whereby the husk is separated from the non-husk seed core and remaining intact seeds. This is most easily achieved by screening (sieving) the milled mixture.

The present invention therefore further relates to processes for obtaining purified psyllium seed husk from a mixture of psyllium seed husk and non-husk seed parts where said mixture is prepared by a dehusking process of the present invention. This purification includes processes comprising the steps of: (a) dividing the dehusked psyllium seed mixture, prepared by a dehusking process as described hereinbefore, into one or more fragments enriched with non-husk material and one or more fragments enriched in husk; and (b) collecting the fragments enriched in psyllium husk. Preferably, the combined fragments enriched in psyllium husk is at least about 95% pure.

Obtaining purified psyllium seed husk may also be achieved by processes comprising the steps of: (a) milling intact psyllium seeds in a mill which causes the husk to be fragmented by collision under conditions whereby the husk is fractured and separated from the non-husk portion of the psyllium seed without substantial breakage and size reduction of the non-husk portion; (b) dividing the dehusked psyllium seed mixture into one or more fragments enriched with non-husk material and one or more fragments enriched with husk; (c) optionally repeating steps (a) and (b); and (d) collecting the fragments enriched in psyllium husk. Preferred are processes wherein the milling is performed by a stud mill.

Division of the husk into the fragments enriched and reduced in non-husk material typically is achieved by procedures which divide material on the basis of density, shape, and/or size. Examples of such procedures include sieving through screens and distribution on gravity tables; or combinations of division methods may be used (e.g., a combination of screening and gravity tables). The dividing of the dehusked psyllium seed mixture into fragments includes, for example, a gradient distribution of husk and non-husk material, whereby the fragments of husk enriched and reduced in non-husk material form a continuum (from most reduced to most enriched), and this continuum is subsequently separated to collect the desired fragments (e.g., separating the end of the gradient continuum enriched in non-husk material from the end reduced in non-husk material). The dividing of the dehusked psyllium seed mixture also includes, for example, methods which result in separation along with the division (e.g., as occurs by sieving). The choice of methods used to divide and separate dehusked psyllium seed mixture may be readily made by one skilled in the art by taking advantage of the differences in the density, size and/or shape of the psyllium seed husk and non-husk material.

Finally, it is preferred for purposes of the present invention to conduct a first milling pass of the intact seeds at a low impact speed of about 15 m/sec or less, preferably within the range of from about 5 m/sec to about 15 m/sec, and more preferably within from about 10 m/sec to about 15 m/sec. This first low impact speed pass is useful for dislodging impurities bound by the seeds. It is desirable, therefore, to collect the psyllium seed husk obtained from this pass separate from the husk obtained from subsequent passes since the proportion of impurities (especially those impurities described in the art as "heavies") is relatively higher for this husk.

The following example further describes and demonstrates an embodiment within the scope of the present invention. The example is given solely for the purpose of illustration and is not to be construed as a limitation of the present invention as many variations thereof are possible without departing from the spirit and scope.

EXAMPLE

An 18 inch (46 cm) diameter Entoleter Centrimil® stud mill (Series 18 Centrimil; sold by Entoleter, Inc.; New Haven, Connecticut) is used to effect psyllium husk removal from intact psyllium seeds. The Centrimil has a 16 inch (41 cm) diameter rotor type M3 and stator type S2. The rotor has 3 rows of ⅜ inch (1 cm) diameter steel pins. The first row has 24 pins at 10 inches (25 cm) diameter; the second row has 36 pins at 12.25 inches (31 cm) diameter; and the third row has 60 pins at 15 inches (38 cm) diameter. The stator is equipped with two rows of ⅜ inch (1 cm) diameter pins. The first row has 30 pins at 11.5 inches (29 cm) diameter; and the second row has 48 pins at 14 inches (36 cm) diameter. The Centrimil is equipped with an electric motor driven variable speed drive.

Multiple stages of impact actions are conducted to effect initial cleaning and subsequent dehusking. Whole Indian psyllium seeds (Plantago ovata) are fed into the Centrimil where the individual seeds are dispersed by the rotor to its periphery. At the rotor periphery, rotating pins impact the seeds which leads them to have further impacts with stationery pins on the stator. The impacted material is then discharged from the Centrimil.

In the first stage, the Centrimil is operated at 650 rpms (maximum and minimum impact speeds of 13 m/sec and 9 m/sec). This first stage effects little husk removal but dislodges impurities bound up by the seeds. The output of the Centrimil is screened on vibrating screen equipment with 25 U.S. standard mesh screen to separate the impurities and small amount of husk removed from the cleaned seeds.

The cleaned seeds from the preceding first stage are then fed by a vibrating feeder at a rate of 0.9 pounds (0.4 kg) per minute into the Centrimil. The rotor is operated at 800 rpms (maximum and minimum impact speeds of 16 m/sec and 11 m/sec). The output from the Centrimil is sieved on 25 U.S. standard mesh vibratory screen to separate husk from the intact seeds and partially and/or wholly dehusked seed cores, which latter mixture is then fed back into the Centrimil. A total of 13 passes through the Centrimil yields 23.4% psyllium husk (excluding any first cleaning stage yield of husk) based on the weight of the incoming seed. This yield of psyllium husk has a purity of 97.9%.

Similarly, effective high purity dehusking of psyllium seeds is achieved as described above by operating the rotor at: 1200 rpms (maximum and minimum impact speeds of 25 m/sec and 16 m/sec) for a total of 7 passes through the Centrimil after the first cleaning stage; and 1400 rpms (maximum and minimum impact speeds of 28 m/sec and 19 m/sec) for a total of 5 passes through the Centrimil after the first cleaning stage.

What is claimed is:

1. A process for cleaning intact psyllium seeds prior to dehusking, said process comprising the steps of:
(a) milling intact psyllium seeds in a mill which produces fragmentation through collision utilizing low impact speeds capable of dislodging impurities bound by the intact psyllium seeds to clean the intact psyllium seeds;
(b) dividing the seed mixture from step (a) into at least one fragment enriched with dislodged impurities and at least one fragment enriched in cleaned intact psyllium seeds; and
(c) collecting the dislodged impurities separated from the cleaned intact psyllium seeds.

2. A process for dehusking psyllium seed, said process comprising the steps of:
(a) cleaning intact psyllium seeds prior to dehusking by the process according to claim 1,
(b) milling the cleaned intact psyllium seeds in a mill which causes the husk to be fragmented by collision under conditions whereby the husk is fractured and separated from the non-husk portion of the psyllium seed without substantial breakage and size reduction of the non-husk portion;

(c) dividing the dehusked seed mixture into at least one fragment enriched with non-husk material and at least one fragment enriched in husk;
(d) optionally repeating steps (b) and (c); and
(e) collecting the psyllium husk separated from the non-husk psyllium seed parts.

3. The process according to claim 2 wherein the cleaned intact psyllium seeds are milled in a stud mill.

4. The process according to claim 3 wherein in step (b) the cleaned intact psyllium seeds are milled under conditions utilizing impact speeds of from about 5 m/sec to about 40 m/sec.

5. The process according to claim 1 wherein the intact psyllium seeds are cleaned in a stud mill.

6. The process according to claim 5 wherein the low impact speeds are within the range of from about 5 m/sec to about 15 m/sec.

7. A process for dehusking intact psyllium seeds, said process comprising the steps of:
(a) milling intact psyllium seeds in a mill which causes the husk to be fragmented by collision under conditions utilizing impact speeds of from about 5 m/sec to less than about 30 m/sec whereby the husk is fractured an separated from the non-husk portion of the psyllium seed without substantial breakage and size reduction of the non-husk portion;
(b) dividing the dehusked seed mixture into at least one fragment enriched with non-husk material and at least one fragment enriched in husk;
(c) repeating steps (a) and (b) for a total of from about 2 to about 13 times; and
(d) collecting the psyllium husk.

8. The process according to claim 7 wherein the psyllium seeds are milled in a stud mill.

* * * * *